(12) United States Patent
Evani

(10) Patent No.: US 7,757,698 B2
(45) Date of Patent: Jul. 20, 2010

(54) INHALER DEVICE

(75) Inventor: Bhanu Murthy Evani, Richmond, VA (US)

(73) Assignee: Philip Morris USA Inc., Richmond, VA (US)

( * ) Notice: Subject to any disclaimer, the term of this patent is extended or adjusted under 35 U.S.C. 154(b) by 879 days.

(21) Appl. No.: 11/644,682

(22) Filed: Dec. 22, 2006

(65) Prior Publication Data
US 2007/0144512 A1 Jun. 28, 2007

Related U.S. Application Data

(60) Provisional application No. 60/753,247, filed on Dec. 22, 2005.

(51) Int. Cl.
*A24D 3/04* (2006.01)
(52) U.S. Cl. ........................ 131/339; 131/341
(58) Field of Classification Search .................. 131/339
See application file for complete search history.

(56) References Cited

U.S. PATENT DOCUMENTS

| | | | |
|---|---|---|---|
| 3,404,692 A | 10/1968 | Lampert | |
| 4,083,372 A | 4/1978 | Boden | |
| 4,274,914 A * | 6/1981 | Keith et al. | 162/109 |
| 4,655,229 A | 4/1987 | Sensabaugh, Jr. et al. | |
| 4,971,078 A * | 11/1990 | Deutsch et al. | 131/335 |
| 4,995,407 A | 2/1991 | Kossiakoff et al. | |
| 6,041,790 A | 3/2000 | Smith et al. | |
| 6,178,969 B1 | 1/2001 | St. Charles | |
| 7,243,659 B1 * | 7/2007 | Lecoultre et al. | 131/341 |
| 2002/0059939 A1 | 5/2002 | Fox | |

FOREIGN PATENT DOCUMENTS

| | | |
|---|---|---|
| DE | 202005005506 | 8/2005 |
| DE | 202005005506 | 9/2005 |
| ES | 2138938 | 1/2000 |
| RU | 2068274 | 10/1996 |

* cited by examiner

*Primary Examiner*—Carlos Lopez
(74) *Attorney, Agent, or Firm*—Connolly Bove Lodge & Hutz LLP

(57) ABSTRACT

An inhaler device comprises a fibrous cylindrical plug with a paper wrapper around the plug. An aromatic substance is applied along the centerline of the plug. Such substance may include eucalyptus oil or menthol. An airtight foil surrounds the paper wrapper and the ends of the cylindrical plug. The inhaler device may be used to ease nasal congestion and quell cough.

7 Claims, 1 Drawing Sheet

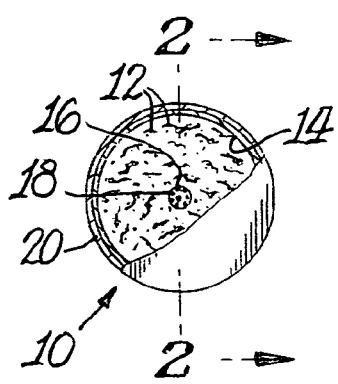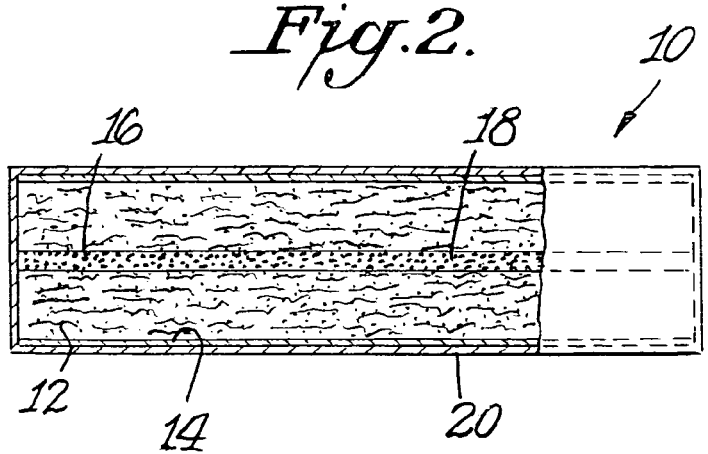

INHALER DEVICE

CROSS REFERENCE RELATED TO APPLICATION

The present application claims the benefit of provisional application Ser. No. 60/753,247, filed Dec. 22, 2005, for all useful purposes, and the specification and drawings thereof are included herein by reference.

BACKGROUND OF THE INVENTION

The present invention relates to an aroma therapy delivery device, and more particularly to an inhaler device which delivers a therapeutic aromatic substance when the device is utilized.

Numerous devices have been proposed for delivering an aromatic substance when inhaled by the user. By way of example, U.S. Pat. No. 4,083,372 describes an inhaler in the size, shape and overall appearance of a cigarette. Aromatic substances including coffee, rum and menthol are packaged in a hermetically sealed soft gel capsule, and when the capsule is punctured the aromatic substance spills onto a wick surrounded by a tubular sheath. The aromatic substance is then inhaled. Other inhalers are used to ease nasal congestion and quell cough. When the aromatic substance delivered by the inhaler is inhaled eucalyptol, this substance works as an expectorant to loosen sticky mucus and make it easier to cough up and out of the chest. Additionally, eucalyptus oil functions in a similar fashion to menthol, obtained from volatile peppermint oil, by acting on receptors in the nasal mucus membranes thereby leading to a reduction in the symptoms of nasal stuffiness.

SUMMARY OF THE INVENTION

Accordingly, one of the objects of the present invention is an inhaler device which delivers an aromatic substance when inhaled by the user.

Another object of the present invention is an inhaler device which is simple in construction, but highly efficient in delivering an aromatic substance in an extremely fresh state.

In accordance with the present invention an inhaler device comprises a fibrous cylindrical plug with a paper wrapper around the plug. A centerline extends through the cylindrical plug from one end thereof to the other, and an aromatic substance is applied at the centerline during formation of the fibrous cylindrical plug. Lastly, an airtight foil surrounds the paper wrapper.

The fibrous cylindrical plug may comprise cellulose acetate fibers including a binder for fusing the cellulose acetate fibers together. The binder may be triacetin, for example. The aromatic substance may be eucalyptus oil or menthol, and the airtight foil may be aluminum.

BRIEF DESCRIPTION OF THE DRAWINGS

Novel features and advantages of the present invention in addition to those mentioned above will be readily apparent to persons of ordinary skill in the art from a reading of the following detailed description in conjunction with the accompanying drawings wherein similar reference characters refer to similar parts and in which:

FIG. 1 is a left end elevational view partially broken away showing an inhaler device, in accordance with the present invention; and FIG. 2 is a side elevational view partially broken away and in cross section taken along line 2-2 of FIG. 1.

DETAILED DESCRIPTION OF THE INVENTION

Referring in more particularity to the drawings, FIGS. 1 and 2 illustrate an inhaler device 10 comprising a fibrous cylindrical plug 12 with a paper wrapper 14 around the plug. The plug 12 may comprise cellulose acetate fibers and a binder which fuses the fibers together. One such binder is triacetin.

A centerline 16 extends through the cylindrical plug 12 from one end thereof to the other, and an aromatic substance 18 is applied at the centerline during formation of the cellulose acetate fibers into the cylindrical plug shape. An airtight foil 20, such as aluminum foil, surrounds the paper wrapper and the ends of the fibrous plug to maintain freshness of the aromatic substance.

Many aromatic substances may be applied at the centerline 16 such as eucalyptus oil and menthol. A Kamich® application may be used to dose molten menthol or eucalyptus oil directly in line onto the center of the fibrous cylindrical plug.

In use, the foil 12 is removed and the device 10 is inhaled to deliver the aromatic substance. When the inhaler is used to ease nasal congestion and quell cough, aromatic substances such as eucalyptus oil or menthol are inhaled and these substances work as an expectorant by loosening sticky mucus which makes it easier to cough up and out of the chest. These aromatic substances act as receptors in the nasal mucus membranes and lead to a reduction of symptoms in nasal stuffiness.

The inhaler device 10 is simply used and discarded and as such the personal hygiene of the inhaler device is far greater when compared to market place devices that warn the consumer not to the use the inhaler more than 28 days or so after first opening the inhaler.

Moreover, the inhaler device 10 of the present invention is different from the hard plastic inhalers which are relatively more expensive and difficult on the environment. Additionally, it is easy to pre-dose differently for different market segments by varying the amount of the aromatic substance applied to the fibrous plug.

What is claimed is:

1. An inhaler device comprising a fibrous cylindrical plug, a paper wrapper around the cylindrical plug, a centerline extending through the cylindrical plug, an aromatic substance on the centerline, and an airtight foil around the paper wrapper.

2. An inhaler device as in claim 1 wherein the fibrous cylindrical plug comprises cellulose acetate fibers.

3. An inhaler device as in claim 2 including a binder fusing the cellulose acetate fibers together.

4. An inhaler device as in claim 3 wherein the binder is triacetin.

5. An inhaler device as in claim 1 wherein the aromatic substance is eucalyptus oil.

6. An inhaler device as in claim 1 wherein the aromatic substance is menthol.

7. An inhaler device as in claim 1 wherein the airtight foil is aluminum foil.

* * * * *